United States Patent [19]
Balodis

[11] Patent Number: 5,965,621
[45] Date of Patent: Oct. 12, 1999

[54] METHODS AND COMPOSITIONS FOR REDUCING OR MAINTAINING BODY WEIGHT IN A MAMMAL

[75] Inventor: Lidija Balodis, Concord, N.H.

[73] Assignee: Allergan, Waco, Tex.

[21] Appl. No.: 09/070,335

[22] Filed: Apr. 30, 1998

Related U.S. Application Data

[63] Continuation-in-part of application No. 08/516,416, Aug. 17, 1995, abandoned.

[51] Int. Cl.$^6$ .................. A61K 31/16; A61K 31/165; A61K 31/44; A61K 31/415
[52] U.S. Cl. .................. 514/616; 514/332; 514/396; 514/397; 514/398; 514/400; 514/401; 514/624; 514/625; 514/629; 514/358
[58] Field of Search .................. 514/396, 397, 514/398, 400, 401, 358, 626, 625, 616, 629, 332; 548/311.1, 327.5, 342.5; 564/197, 193

[56] References Cited

U.S. PATENT DOCUMENTS

| | | | |
|---|---|---|---|
| 4,371,540 | 2/1983 | Lee et al. .................. | 548/327.5 X |
| 4,568,683 | 2/1986 | Suga et al. .................. | 514/358 |
| 4,571,401 | 2/1986 | Picciola et al. .................. | 514/332 |
| 4,576,958 | 3/1986 | Wexler .................. | 514/400 |
| 4,632,930 | 12/1986 | Carini et al. .................. | 514/365 |
| 4,937,266 | 6/1990 | Tomikawa et al. .................. | 514/616 |
| 4,954,515 | 9/1990 | Suto .................. | 514/398 |
| 5,304,654 | 4/1994 | Kagiya et al, II .................. | 548/327.5 |
| 5,342,959 | 8/1994 | Bexlin et al. .................. | 548/327.5 |

FOREIGN PATENT DOCUMENTS

| | | | |
|---|---|---|---|
| 0316967 | 5/1989 | European Pat. Off. .................. | 548/327.5 |
| 0373630 | 6/1990 | European Pat. Off. .................. | 548/327.5 |
| 94-11348 | 5/1994 | WIPO .................. | 548/327.5 |

OTHER PUBLICATIONS

Merck Index, 11$^{th}$ Edition, p. 110, Item #6962 (1989).

*Primary Examiner*—Floyd D. Higel
*Attorney, Agent, or Firm*—Frank J. Uxa

[57] ABSTRACT

A method for reducing or maintaining the level of adipose tissue formation in a mammal includes the step of administering a pantethine composition to the mammal in an amount and for a period of time sufficient to achieve a desired body weight. Compositions useful in carrying out the method include an adipose modulating amount of the pantethine component and a pharmaceutically acceptable carrier.

20 Claims, No Drawings

METHODS AND COMPOSITIONS FOR REDUCING OR MAINTAINING BODY WEIGHT IN A MAMMAL

RELATED APPLICATION

This application is a continuation-in-part of application Ser. No. 08/516,416 filed Aug. 17, 1995 now abandoned, the disclosure of which is hereby incorporated by reference in its entirety herein.

FIELD OF THE INVENTION

The present invention relates to the control of adiposity in a mammal through modulation of triglyceride metabolism. More specifically, it relates to the control of body weight through administration of pantethine or a hypolipidemic pantethine derivative to the mammal.

BACKGROUND OF THE INVENTION

In humans, excessive adiposity, or body weight, is a problem bordering on obsession in certain populations, particularly in Western cultures. Popular weight loss methods extend from behavioral regimes to pharmaceutical therapies, encompassing a vast spectrum of diets, diet aids, exercise programs and alleged miracle cures. However, among these methods, very few are specifically directed toward modulating the known biochemical processes of adipose synthesis and metabolism.

According to one prevailing hypothesis, most mammals (including humans) produce adipose tissue through adipose tissue lipoprotein lipase (ATLPL) hydrolysis of fatty acids from the triglycerides of circulating triglyceride-rich lipoprotein. The released fatty acids are taken up by adipocytes, converted to triglycerides, and stored. Thus, the so-called "lipoprotein lipase hypothesis" holds that ATLPL particulates in the preferential production of adipose tissue from excess fat calories (see, e.g., Isselbacher et al. "Harrison's Principles of Internal Medicine", Vol. 1, Part 5, p. 448 (McGraw-Hill, 1994)). Hypertriglyceremia and hyperlipoproteinemia conditions have been associated with obesity through excessive hepatic secretion of triglycerides in response to increased levels of free fatty acids in plasma (id. at p. 449).

To date, the common pharmaceutical approaches to weight management have been principally palliative, involving administration of anorexiants (generally amphetamine-like agents to suppress appetite) or thyroid hormone (where obesity is related to hyperthyroidism) (id. at p. 551). Neither approach is targeted to the biochemical pathways associated with adipose formation.

In contrast, research regarding the pharmaceutical control of excessive lipid levels in serum and body organs (particularly the liver and vessels of the cardiovascular system) has been extensive in recent years. For example, since about 1980, pharmaceutical hypolipidic agents began to be tested in animals and humans for their effect on circulating levels of lipids and cholesterol for treatment of diseases of the liver and cardiovascular system. One such hypolipidic agent studied is pantethine, a disulfide linked pantetheine dimer in which each dimeric unit includes pantothenic acid (vitamin $B_3$) linked to $\beta$-mercaptoethylene. Pantethine has a molecular weight of 554.7 g/mol and has the following structure:

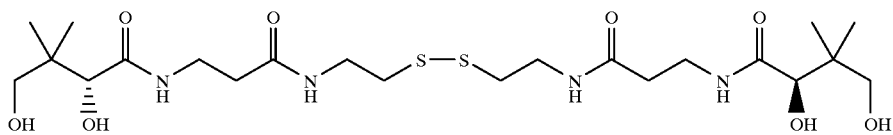

Pantethine is an intermediate in the metabolic pathway for biosynthesis of acetyl coenzyme A (CoA).

Pantethine has been used clinically and/or experimentally to deliver cysteamine to reduce plasma and pituitary prolactin in humans (Jeitner and Oliver, J. Endocrinol., 124: 397–402, 1990), to reduce total serum cholesterol and triglyceride levels in human patients suffering from, or at risk for, cardiac disease (Arsenic et al., Acta. Biomed. Ateneo Parmense, 58: 143–152, 1987; U.S. Pat. No. 4,571, 401 to Picciola et al.), to limit hepatic lipid storage in chickens (Hsu et al, Poult. Sci., 66: 280–286, 1987), to limit hepatic fibrosis in humans (U.S. Pat. No. 4,937,266 to Tomikawa et al.), and to inhibit phase separation of ocular lens proteins for treatment of cataract conditions. Pantethine has also been shown to be atoxic in animals and humans (see, e.g., Donati et al., Clin. Nephrol., 25: 70–74, 1986; Arsenic et al., supra). A pantetheine derivative, pantetheine-S-sulfonic acid, has been employed to improve lipid metabolism (U.S. Pat. No. 4,568,683 to Suga et al.).

However, to date, pantethine per se has not been widely used to treat abnormal lipid accumulation and metabolism in humans (Harrison's Principals of Internal Medicine, supra at pages 450 and 1112–1113), and has not been suggested as a possible pharmaceutical agent of use in the control of excessive adipose deposition in animals or humans.

A continuing need exists for effective compositions and treatment regimens for the control of excessive adipose deposition in mammals.

SUMMARY OF THE INVENTION

In accordance with one aspect of the present invention, a method for reducing the level of adipose tissue in a mammal is provided which includes the step of administering a pantethine component selected from the group consisting of pantethine, hypolipidic pantethine derivatives and mixtures thereof to the mammal in a dosage sufficient to decrease or reduce the metabolism of fatty acids to triglycerides therein. As used herein, the term "hypolipidic pantethine derivative" refers to a pharmaceutically acceptable compound structured similarly to pantethine in which at least one group, for example, hydroxy group, carbonyl group and/or amino group, is replaced by another group such that the compound has at least a portion, for example, at least about 30% or about 50%, preferably at least about 70% or about 90%, of pantethine's hypolipidic activity. Compounds in which at least one hydroxy group of pantethine is replaced are preferred pantethine derivatives.

According to another aspect of the present invention, a method for maintaining the body weight of a mammal by controlling the levels of adipose deposits therein below a given level includes the step of administering a pantethine component selected from pantethine, hypolipidic pantethine derivatives and mixtures thereof to the host in a dosage sufficient to decrease or reduce the metabolism of fatty acids to triglycerides therein.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

According to a preferred method of the invention, a mammal in need of controlling or reducing adipose tissue formation to achieve or maintain a desired body weight receives an adipose modulating amount of a pantethine component selected from pantethine, hypolipidic pantethine derivatives and mixtures thereof, for example, by a parenteral route of administration. The term "adipose modulating amount" as used herein denotes an amount of the pantethine component, that is pantethine and/or hypolipidic pantethine derivative(s), that will detectably decrease or reduce, preferably by at least 10%, metabolism by the mammal of fatty acids to circulating triglycerides. The term "hypolipidic pantethine derivative" as used herein denotes a pharmaceutically acceptable derivative of pantethine that will detectably decrease or reduce metabolism by the mammal of fatty acids to circulating triglycerides when administered to the mammal as described herein.

Methods for detecting levels of triglycerides in a body fluid (e.g., blood or plasma) are well-known in the art, such as affinity chromatography or, conveniently, commercially available test kits, such as the TRIGLYCERIDE-G Test sold by Wako, of Japan. Preferably, conventional tests to determine blood levels of, for example, total cholesterol, HDL-cholesterol, apo A-1 and B lipoprotein, and white blood cell levels are performed periodically to monitor the general health of the mammal during treatment.

Suitable subjects for the method of the invention generally are mammals who suffer from excessive adiposity or whose health otherwise requires that they lose body weight. Particularly suitable subjects are those mammals who are suffering from a pathologic condition for which pantethine is believed to have therapeutic efficacy, such as hyperlipidemia. However, pathologically normal mammals will also benefit from the methods of the invention.

An adipose modulating effect can be achieved by administration of the pantethine component, that is pantethine and/or hypolipidic pantethine derivative(s), in dosages ranging from as little as 100 mg/day up to the limit of the mammal's tolerance to the pantethine component. Generally, tolerance to pantethine can be expected to be relatively high. For example, the compound is reported to have an $LD_{50}$ ranging from 1690 mg/kg by intravenous injection in rats to >10,000 mg/kg by oral administration in mice. In this respect, "$LD_{50}$" refers to the dosage of a compound which is lethal to 50% of the treated population. The $LD_{50}$ for a compound is commonly determined in a rodent species by administration of the compound to a set population under controlled conditions, which value can then be extrapolated to other mammalian species by factors such as body mass. Those of ordinary skill in the art will be readily able to determine upper levels of tolerance to the pantethine component in a particular mammal species.

In humans, the pantethine component, for example, pantethine, preferably is administered in amounts ranging from, or equivalent to, about 400 mg/day to 2000 mg/day (based on adult body weight of about 60 kg), most preferably about 600 mg/day to 1200 mg/day, with greater amounts being administered if taken orally than if taken by other parenteral routes, such as by intramuscular or intravascular injection. However, for purposes of patient comfort and minimization of tissue trauma from invasive means of delivery, the pantethine component preferably is administered orally. Within these parameters, doses of greater than about 1000 mg/day are preferred for adipose tissue reduction, while doses of less than about 1000 mg/day are preferred for maintenance of body weight below a given level. Further, those of ordinary skill in the art will be able to readily determine the suitable, equivalent dosage range for use in a non-human mammal species, in whom the pantethine component is preferably administered as a dietary supplement. In all mammals, the actual dosage administered will vary depending on the age, health and presenting condition of the mammal, which variables may be readily determined by one of ordinary skill in the art.

A suitable animal model for determining the efficacy of various quantities of pantethine and/or hypolipidic pantethine derivative(s) administered according to the present invention is the rodent, particularly the mouse. Testing preferably is carried out in two groups: a control group receiving saline injections or placebo as a dietary supplement, and a test group. Body weight (in particular, abdominal fat) and plasma lipid levels are determined before and after treatment. Controlled levels of standard animal fee are supplied to both groups at regular intervals throughout the test period or, for greater control of caloric intake, both groups are fed intravenously. Alternatively, both groups can fast for equal periods of time during treatment. Activity in both groups is restricted by, for example, maintaining each animal in a separate cage of equal size.

The test group receives daily doses of the pantethine component is question at amounts to be tested for adipose modulating effects by the same route that the placebo is received in the control group. Body weight will be monitored during a test period of at least about 1 week. Reduction of circulating levels of triglycerides should be detected within about 24 hours of the first dosing. Monitoring of plasma lipid levels and other indicia of health (e.g., serum uric acid) in both groups during treatment will be indicative of the impact of weight reduction by the method of the invention at differing levels of the pantethine component over differing periods of time.

The time course of treatment required will vary widely depending on the reducing goals for the mammal. However, weight loss should be monitored periodically (e.g., every two weeks) to determine if the dosage of the pantethine component is adequate to meet the goals or if it should be increased. Of course, the best results will be obtained through combination of the method of the invention with an appropriate program of diet and exercise.

For use in the invention, pantethine may be formulated as described above or obtained in commercially available quantities (for example, from Sigma Chemical) to be administered in dosages and forms according to the invention.

For oral administration, hypolipidic pantethine derivatives are known which may be more palatable to the mammal than pure pantethine. Exemplary hypolipidic pantethine derivatives which can be employed according to the invention include esters of pantethine; acid (organic and inorganic) addition salts of pantethine; metal, ammonium and amine salts of pantethine; and the like pantethine derivatives. The presently useful pantethine derivatives are pharmaceutically acceptable and have at least a portion, preferably a major portion, of the hypolipidic activity of pantethine. Useful derivatives of pantethine can be produced using methods which are conventional and well known in the art. For example, pantethine can be reacted with an organic acid, an organic acid halide or an organic acid anhydride at effective esterification reaction conditions to produce suitable pantethine esters. Other approaches, for example, through the use of enzymes, can be used to produce pantethine esters. One or more than one of the hydroxy groups of pantethine can be esterified, and all such compounds are included within the scope of the present invention provided that they are pharmaceutically acceptable and have hypolipidic activity.

Conventional salt forming reactions can be employed to produce the presently useful pantethine salt derivatives. Examples of such pantethine salts include alkali metal salts, alkaline earth metal salts, aluminum salts, ammonium salts, amine salts, acid salts and the like. Addition salts with organic and inorganic acids may be employed. Useful organic acids include, for example, carboxylic or sulfonic acids, and may contain other functional groups such as for instance hydroxy, amino, etc. Specific useful organic acids include the following: formic, acetic, propionic, glycolic, lactic, citric, ascorbic, fumaric, maleic, oxalic, pamoic, succinic, tartaric, phenylacetic, benzoic, p-aminobenzoic, anthranilic, p-hydroxybenzoic, salicylic, malic, methanesulfonic, ethanedisulfonic, glucuronic, glutamic acids and others. Useful inorganic acids include, for example, hydrochloric, hydrobromic, hydroiodic, sulfuric, phosphoric, perchloric acids and others. Examples of such derivatives are described in U.S. Pat. No. 4,571,401 and U.S. Pat. No. 4,288,441, the disclosures of which are incorporated herein by reference.

All forms, e.g., isomers, stereoisomers, enantiomers, tautomers and the like, of the hypolipidic pantethine derivatives which are pharmaceutically acceptable and have hypolipidic activity are useful in accordance with the present invention.

The pantethine component is administered in a pharmaceutically acceptable form. To this end, the pantethine and/or hypolipidic pantethine derivative(s) can be formulated in a pharmaceutically acceptable carrier and in a variety of forms depending on the chosen route of administration. For example, the pharmaceutical carrier employed may be either a solid, liquid, or time release (see Remington's Pharmaceutical Sciences, Mack Publishing Co., Easton, Pa., 16th ed., 1982, incorporated herein by reference). Exemplary solid carriers are lactose, terra alba, sucrose, Di-Pac, talc, gelatin, agar, pectin, acacia, magnesium stearate, stearic acid, starch, microcrystalline cellulose, polymer hydrogels and the like. Exemplary liquid carriers are syrup, peanut oil, and olive oil and the like emulsions. Similarly, the carrier are syrup, peanut oil, and olive oil and the like emulsions. Similarly, the carrier or diluent may include any time delay material well known to the art, such as glyceryl monostearate or glyceryl distearate alone or with a wax, microcapsules, microspheres, liposomes, and hydrogels. A particularly suitable means to extend the in vivo half-life of the pantethine component is conjugation to polyethylene glycol (PEG).

A wide variety of pharmaceutical forms can be employed. Thus, when using a solid carrier the preparation can be tableted, placed in a hard gelatin capsule in powder or pellet form, or in the form of a troche, lozenge or suppository. When using a liquid carrier the preparation can be in the form of a liquid, such as an ampule, or as an aqueous or nonaqueous liquid suspension. Liquid dosage forms typically also require pharmaceutically acceptable preservatives and the like, all of which are known to those of ordinary skill in the art.

The invention is further illustrated by the following non-limiting examples.

EXAMPLE 1—TABLET

A tablet having the following composition is prepared using a tableting machine.

| | |
|---|---|
| Pantethine | 900 mg |
| Lactose | 600 mg |
| Glucose | 500 mg |
| Magnesium stearate | 20 mg |

EXAMPLE 2—TABLET

A tablet having the following composition is prepared using a tableting machine.

| | |
|---|---|
| Pantethine | 900 mg |
| Starch | 1100 mg |
| Magnesium stearate | 20 mg |

EXAMPLE 3—CAPSULE

A homogeneous composition having the following composition is prepared and formed into granules using an extruder. The granules are dried and encapsulated in a conventional gelatin capsule.

| | |
|---|---|
| Pantethine | 900 mg |
| Lactose | 250 mg |
| Crystalline cellulose | 250 mg |
| Hydroxypropylcellulose | 600 mg |

EXAMPLES 4–6

Examples 1 to 3 are repeated except that an ester of pantethine with 3-pyridineacetic acid is used in place of pantethine.

EXAMPLES 7–9

Examples 1 to 3 are repeated except that pantethine acetate addition salt is used in place of pantethine.

EXAMPLES 10–12

Examples 1 to 3 are repeated except that pantethine hydrochloride is used in place of pantethine.

EXAMPLES 13–15

Examples 1 to 3 are repeated except that the disodium salt of pantethine is used in place of pantethine.

While this invention has been described with respect to various specific examples and embodiments, it is to be understood that the invention is not limited thereto and that it can be variously practiced within the scope of the following claims.

What is claimed is:

1. A method for reducing the body weight of a mammal comprising the step of administering a pantethine composition selected from the group consisting of pantethine, hypolipidic pantethine derivatives and mixtures thereof to the mammal in an amount and for a period of time sufficient to reduce the body weight of the mammal, the hypolipidic pantethine derivatives being selected from the group consisting of pantethine esters in which one or more hydroxy groups of pantethine are esterified with an organic acid, organic and inorganic acid addition salts of pantethine, metal salts of pantethine, ammonium salts of pantethine, amine salts of pantethine and mixtures thereof and are effective when administered to the mammal to detectably reduce metabolism by the mammal of fatty acids to circulating triglycerides.

2. The method according to claim 1 wherein the pantethine composition is administered orally to the mammal.

3. The method according to claim 2 wherein the pantethine composition is in tablet form.

4. The method according to claim 1 wherein the pantethine component includes a hypolipidic pantethine derivative selected from the group consisting of pantethine esters in which one or more hydroxy groups of pantethine are esterified, organic and inorganic acid addition salts of pantethine, metal salts of pantethine, ammonium salts of pantethine and amine salts of pantethine.

5. The method according to claim 1 wherein the mammal is a human adult with excessive adiposity.

6. The method according to claim 5 wherein the pantethine composition is administered in an amount of about 600 mg/day to 1200 mg/day.

7. The method of claim 1 wherein the hypolipidic pantethine derivatives are effective when administered to the mammal to reduce metabolism by the mammal of fatty acids to circulating triglycerides by at least 10%.

8. The method of claim 7 wherein the pantethine composition is pantethine.

9. A method for maintaining the body weight of a mammal comprising the step of administering a pantethine composition selected from the group consisting of pantethine, hypolipidic pantethine derivatives and mixtures thereof to the mammal in an amount and for a period of time sufficient to maintain the body weight of the mammal at a preselected level, the hypolipidic pantethine derivatives being selected from the group consisting of pantethine esters in which one or more hydroxy groups of pantethine are esterified with an organic acid, organic and inorganic acid addition salts of pantethine, metal salts of pantethine, ammonium salts of pantethine, amine salts of pantethine and mixtures thereof and are effective when administered to the mammal to detectably reduce metabolism by the mammal of fatty acids to circulating triglycerides.

10. The method according to claim 9 wherein the pantethine composition is administered orally to the mammal.

11. The method according to claim 10 wherein the pantethine composition is in tablet form.

12. The method according to claim 9 wherein the pantethine component includes a hypolipidic pantethine derivative selected from the group consisting of pantethine esters in which one or more hydroxy groups of pantethine are esterified, organic and inorganic acid addition salts of pantethine, metal salts of pantethine, ammonium salts of pantethine and amine salts of pantethine.

13. The method according to claim 9 wherein the mammal is a human adult.

14. The method according to claim 13 wherein the pantethine composition is administered in an amount is about 600 mg/day to 1200 mg/day.

15. The method of claim 9 wherein the hypolipidic pantethine derivatives are effective when administered to the mammal to reduce metabolism by the mammal of fatty acids to circulating triglycerides by at least 10%.

16. The method of claim 9 wherein the pantethine composition is pantethine.

17. The method according to claim 16 wherein the pantethine composition is administered in an amount of about 600 mg/day to 1200 mg/day.

18. A composition for modulating the level of adipose tissue in a mammal comprising an adipose tissue modulating amount of a pantethine composition selected from the group consisting of pantethine, hypolipidic pantethine derivatives and mixtures thereof, and a pharmaceutically acceptable carrier, the hypolipidic pantethine derivatives being selected from the group consisting of pantethine esters in which one or more hydroxy groups of pantethine are esterified with an organic acid, organic and inorganic acid addition salts of pantethine, metal salts of pantethine, ammonium salts of pantethine, amine salts of pantethine and mixtures thereof and are effective when administered to the mammal to detectably reduce metabolism by the mammal of fatty acids to circulating triglycerides.

19. The composition of claim 18 comprising about 600 to 1200 mg of the pantethine composition.

20. The composition of claim 19 wherein the pantethine composition is pantethine.

\* \* \* \* \*